United States Patent [19]

Duranleau et al.

[11] Patent Number: 5,182,025

[45] Date of Patent: Jan. 26, 1993

[54] METHOD OF NEUTRALIZING POLYOL CATALYSTS AND PRODUCTS

[75] Inventors: Roger G. Duranleau, Georgetown; Martin J. Plishka; Michael Cuscurida, both of Austin, all of Tex.

[73] Assignee: Texaco Chemical Company, White Plains, N.Y.

[21] Appl. No.: 891,070

[22] Filed: Jun. 1, 1992

[51] Int. Cl.$^5$ ............................................. B01D 15/04
[52] U.S. Cl. .................................. 210/681; 210/685; 210/660; 568/868
[58] Field of Search ...................... 210/660, 681, 685; 568/868

[56] References Cited

U.S. PATENT DOCUMENTS 4,385,121 5/1983 Knowlton ........................... 210/611
4,477,355 10/1984 Liberti et al. ....................... 210/665
4,539,761 9/1985 Habermehl .......................... 210/925
4,581,470 4/1986 Hoy et al. ........................... 560/189
4,659,772 4/1987 Hoy et al. ........................... 524/755
4,747,954 5/1988 Vaughn et al. ..................... 210/670

Primary Examiner—Stanley S. Silverman
Assistant Examiner—Cynthia L. Nessler
Attorney, Agent, or Firm—Jack H. Park; Kenneth R. Priem; Cynthia L. Kendrick

[57] ABSTRACT

Disclosed is a method for removing potassium from polyol and alkoxylated alkyl phenol products and neutralizing soluble base catalysts which comprises using a partially spent ion exchange resin which no longer meets the purity requirements for the production of MTBE, ETBE or TAME, washing the catalyst, mixing it with the polyol or alkoxylated alkylphenol in an acid/base ratio of about 7/1 to 10/1, for a period of hours and removing the filtrate.

7 Claims, No Drawings

METHOD OF NEUTRALIZING POLYOL CATALYSTS AND PRODUCTS

BACKGROUND OF THE INVENTION

1. Field of the Invention

This invention relates to an efficient method for neutralizing an alkoxylation catalyst. More particularly, this invention relates to a new use for partially spent ion exchange resins and an environmentally attractive method of neutralizing alkoxylation catalysts and removing potassium ions from polyol and alkoxylated alkyl phenol products. Example 2 demonstrates a reduction in potassium to less than 1 ppm.

This method is not only efficient and inexpensive, but also reduces problems inherent in disposal of a partially depleted acidic resin catalyst and reduces the impact on the environment of disposing of filter cakes which remain after using currently available methods to neutralize soluble base catalysts used in alkoxylation reactions.

2. Description of Related Art

One of the most critical fields of study in industrial chemical processes is that of devising methods to remove impurities from products and effluent streams at low cost and, also, to avoid having to dispose of chemical compositions such as catalysts which are still partially active. Plants producing or using basic materials such as ammonia, organic amines, alkali salts or caustic have waste streams that often need to be neutralized. The manufacture of polyols and alkyl phenol alkoxylates presents such a problem.

Polyols and alkyl phenol alkoxylates ar usually manufactured by the base catalyzed addition of propylene oxide or ethylene oxide to various initiators. The catalyst used is potassium hydroxide or another soluble base. The amount of potassium in the final product is critical in order to maintain control of downstream reactions. With one procedure, the catalyst is removed by neutralizing the base with a small excess of $H_2SO_4$, absorbing the formed salt, (usually $K_2SO_4$) with magnesium silicate, then filtering the product after heating to reduce the viscosity. The filter cake is then disposed of in a land fill.

In the past ion exchange resins have been used to produce polyols and, in fact, worked well. The disadvantage involved the fact that the solution used to regenerated the resin is considered a hazardous waste and is expensive to get rid of properly.

The use of ion exchange resins for removal of magnesium and noncarbonate minerals from water is known in the field of water treatment or water softening. The cost and frequency of regeneration are principal disadvantages. The ion-exchange material generally used in softening water are styrene-divinyl benzene copolymers. *Kirk-Othmer Encyclopedia of Chemical Technology*, 8, 70 and 24, 425 (1982).

Another aspect of the background for this invention is that the current transition to unleaded fuels in the U.S. has caused a demand for the addition of oxygenates into gasoline which has lead to the development of methyl-tert-butylether as a gasoline additive. The demand for MTBE has caused it to be the fastest growing chemical of the 80's and the demand will grow rapidly in the 90's. Chemical Business, January 1992, p.24. MTBE and other chemicals such as ethyl-tert-butylether (ETBE) and tert-amyl methylether (TAME) are made by the addition of alcohol to an olefin catalyzed by a sulfonic acid ion exchange resin.

The consumption of MTBE is currently about 180,000 barrels per day and could be as high as 670,000 barrels per day by the year 2000. Ibid, p. 25. Another reference indicates the demand would reach 1.2 million barrels per day by the year 2000. (Chemical Week, Nov. 20, 1991, p. 36.)

Due to the demand for high productivity the ion exchange catalyst is used until reduced activity makes it more reasonable to exchange it for a fresh catalyst. This corresponds to a point of about 70-90%, and generally about 85%, of its original activity. This means there are enormous amounts of used catalyst that must be disposed of. Disposal of this partially spent catalyst gives rise to environmental concerns and often requires some sort of permit. It would be extremely efficient from a commercial and environmental viewpoint to accomplish a desirable goal using this partially spent catalyst, reduce the remaining activity of the resin so that disposal of it is not as objectionable and eliminate the production of a filter cake which requires disposal.

It would be a distinct advance in the art if an inexpensive means were available for neutralizing an alkoxylation catalyst and reducing impermissible levels of potassium in polyol and alkoxylated alkyl phenol products. It would be advantageous if this could be accomplished with a substance which to this point has had to be discarded while activity remains due to purity requirements of the primary product, i.e. MTBE, ETBE or TAME. To remove potassium from polyols and alkoxylated alkyl phenols with a partially spent catalyst, that normally entails disposal problems, and eliminate the neutralization of potassium hydroxide and the resulting filter cake would be quite efficient in every respect.

SUMMARY OF THE INVENTION

It is the purpose of this invention to utilize a very important development in industrial chemistry for the purpose of removing alkali metals from polyol and alkoxylated alkyl phenol products at a very low cost.

In accordance with the foregoing the instant invention describes a method to utilize the remainder of a partially spent MTBE ion-exchange resin to neutralize a potassium hydroxide polyol catalyst and remove impermissible levels of potassium from the product, thus eliminating the current tedious magnesium silicate treatment, as well as the cost of the adsorbent and, further, eliminate the cost for disposal of a filter cake. In the method of this invention, when the partially spent MTBE resin has lost its effectiveness in removing potassium, it is disposed of in the same manner in which it is disposed of now, except it is more completely spent. But the fact that this method has eliminated the need for the tedious method of neutralization described above and its inherent filter cake would be a great contribution environmentally.

DESCRIPTION OF THE PREFERRED EMBODIMENT

In the method of this invention up to about 98% of the potassium impurities, are removed from polyols and alkoxylated alkyl phenol products using a partially spent ion-exchange resin used in the production of MTBE which may require a permit to dispose of in some locations. Finished products are required to contain no more than 1 ppm potassium in order to maintain control of downstream reactions and by the method disclosed herein the levels of potassium can be reduced to substantially less than 1 ppm.

The feedstock comprises products containing unacceptable levels of potassium. These products may contain not only potassium, but other ions, including, but not limited to sodium, cesium, magnesium, barium, and aluminum.

The catalyst is an ion-exchange resin of the type used in the production of methyl tertiary butyl ether, ethyl tertiary butyl ether and tertiary amyl methyl ether. Catalysts of this type are generally characterized by insoluble cross-linked polymers and often contain sulfuric acid groups. Examples include Amberlite®IR-118, Amberlite®IR-120, Amberlyst®15, Amberlyst®120 and Dowex®50 resins.

Dowex® is the tradename for a series of strongly acid synthetic ion exchange resins manufactured by Dow Chemical Co. made from styrene-divinylbenzene copolymers, having a large number of ionizable or functional groups attached to this hydrocarbon matrix. These functional groups determine the chemical behavior and types of ion-exchange resins. The Amberlite® and Amberlyst® resins are strongly acidic resins which are supplied by the Rohm and Haas Chemical Co.

As mentioned, due to the demand for high productivity, the ion exchange resins still have about 85% of the original capacity at the point at which they are taken out of service. The "used MTBE resins" described herein are almost as effective for neutralizing and purifying polyols as unused resins purchased new, which are considerably more expensive. In fact, the used resin is about 85% as effective as a new ion exchange resin.

The examples demonstrate the method of the invention for neutralization of a catalyst and removal of potassium ions. Example 2 demonstrates that the ppm of potassium can be reduced to 0.2 ppm, much less than the limit of 1 ppm. It is understood that the examples given are only for illustration and that the invention is not intended to be limited thereby.

EXPERIMENTS 1 AND 2

Examples 1 and 2 demonstrate the use of discarded Dowex®50 resin, employed in the production of MTBE, to neutralize polyol and alkoxylated alkyl phenol products which have impermissible levels of potassium ions.

The results showed that the recovered Dowex®50 resin readily removed potassium from alkaline PPG-200 and the nine-mole ethoxylate of octyl phenol after a two to three hour treatment at 75° C. using a 7/1 to 10/1 acid/base ratio. The treated products had an off-yellow color which, it is believed, could have been due to the resin being used as received.

The results are given in Table I:

TABLE I

| Reclaimed Dowex ®50 in Neutralization of PPG-200 and t-Octyl Phenol.9EO | | |
|---|---|---|
| Sample No. | EX. 1 | EX. 2 |
| Charge | 6740-56 | 6740-80 |
| Alkaline PPG~200, g[a] | 1000 | — |
| Alkaline t-OP.9EO, g[b] | — | 1000 |
| Water, g | 20 | 20 |
| Recovered Dowex ®50, g[c] | 52 | 72 |
| Details of Neutralization | | |
| Temperature, °C. | 75 | 75 |
| Time, hr. | 2 | 3 |
| Eq. acid/base | 7 | 10 |
| Properties | | |
| Acid no., mg KOH/g | 0.015 | 0.017 |
| Water, wt % | 0.005 | 0.08 |
| pH in 10:6 isopropanol-water | 6.8 | 6.9 |
| Sodium, ppm | 1.3 | 0.2 |
| Potassium, ppm | 10.0 | 0.2 |
| Appearance | Off yellow | Off yellow |

[a]Contained 470 ppm potassium
[b]Contained 350 ppm potassium
[c]Contained 1.87 meq/g H+

What is claimed is:

1. A method for removing potassium from polyol products which comprises using a partially spent insoluble cross-linked polymeric ion exchange resin catalyst possessing 60-90% of its original activity, washing the partially spent catalyst, mixing the polyol product with the partially spent catalyst in an acid/base ratio of 7/1 to 10/1, for a period of 1 to 5 hours and removing the filtrate.

2. The method of claim 1 wherein the catalyst has about 70-85% of its original activity.

3. The method of claim 1 wherein the catalyst has about 80-85% of its original activity.

4. The method of claim 1 wherein the polyol is a polypropylene glycol having a molecular weight of from about 200 to about 2000.

5. A method for removing potassium from an alkoxylated alkyl phenol product which comprises using a partially spent insoluble cross-linked polymeric ion exchange resin catalyst possessing 60-90% of its original activity, washing the partially spent catalyst, mixing the polyol product with the partially spent catalyst in an acid/base ratio of 7/1 to 10/1, for a period of 1 to 5 hours and removing the filtrate.

6. The method of claim 5 wherein the catalyst has about 80-85% of its original activity.

7. The method of claim 1 wherein the alkoxylated alkyl phenol was t-octyl phenol.

* * * * *